United States Patent [19]
Yves et al.

[11] Patent Number: 5,338,689
[45] Date of Patent: Aug. 16, 1994

[54] METHOD AND CARD FOR DETECTING ANTIGENS AND/OR ANTIBODIES

[75] Inventors: Lapierre Yves, Dullins, France; Dieter Josef, Fribourg, Switzerland; Jean Adam, Meyriez, Switzerland; Susanne Greber-Widmer, Herrenschwanden, Switzerland

[73] Assignee: Stiftung fur diagnostische Forschung, Murten, Switzerland

[21] Appl. No.: 969,532

[22] Filed: Oct. 30, 1992

Related U.S. Application Data

[63] Continuation of Ser. No. 684,459, Apr. 11, 1991, abandoned, which is a continuation of Ser. No. 122,152, Nov. 11, 1987, abandoned.

[30] Foreign Application Priority Data

Aug. 24, 1987 [CH] Switzerland ............... 3240/87

[51] Int. Cl.$^5$ .............. G01N 33/537; G01N 33/538; G01N 33/555; G01N 33/558
[52] U.S. Cl. ...................... 436/518; 422/58; 422/61; 422/68.1; 422/102; 435/7.2; 435/7.25; 436/165; 436/514; 436/519; 436/520; 436/524; 436/527; 436/528; 436/529; 436/534; 436/536; 436/538; 436/541; 436/805; 436/808; 436/809; 436/824
[58] Field of Search .............. 422/58, 61, 72, 68.1, 422/99, 102, 104; 436/164, 165, 514, 518, 519, 520, 524, 527, 528, 529, 534, 536, 538, 541, 805, 808, 809, 824; 435/7, 2, 7.25

[56] References Cited

U.S. PATENT DOCUMENTS

| | | | |
|---|---|---|---|
| 3,492,396 | 1/1970 | Dalton | 422/58 |
| 3,718,133 | 2/1973 | Perry et al. | 422/102 |
| 3,876,376 | 4/1975 | Bauman et al. | 422/102 |

(List continued on next page.)

FOREIGN PATENT DOCUMENTS

| | | |
|---|---|---|
| 39195 | 11/1981 | European Pat. Off. . |
| 0194156 | 9/1986 | European Pat. Off. . |
| 1005759 | 4/1957 | Fed. Rep. of Germany . |
| 2236181 | 1/1975 | France . |
| 2554240 | 5/1985 | France . |
| 8502010 | 8/1986 | France . |
| 0194212 | 9/1986 | France . |
| 0224439 | 6/1987 | France . |
| 2017910 | 10/1979 | United Kingdom . |
| 8300296 | 3/1983 | World Int. Prop. O. ......... 422/104 |

OTHER PUBLICATIONS

Yapa, et al., "Use of papain treatment of NR latex to produce superior-quality rubbers," *Chemical Abstracts* 94 (18):59 May 4, 1981.

(List continued on next page.)

*Primary Examiner*—Toni R. Scheiner
*Assistant Examiner*—Christopher L. Chin
*Attorney, Agent, or Firm*—Nikaido, Marmelstein, Murray & Oram

[57] ABSTRACT

A method of detecting target antibodies or antigens by reaction with specific binding partners thereto is disclosed. One of the target or the binding partner is bound to a carrier, and the other is unbound. The complex between the target and the binding partner, with one being carrier-bound, forms an optically detectable binding complex. A microreaction vessel having an upper portion, a transition portion and a lower portion is utilized, wherein the upper portion has a greater diameter or width than the lower portion, and the transition portion is situated between the upper portion and the lower portion, and is funnel shaped. The microreaction vessel contains a slurry or suspension of inert particles, and unbound target or binding partner thereto. A solution of the carrier bound target or binding partner thereto is added to the vessel, which is then centrifuged to produce an optical determination of the target. A strongly positive reaction is indicated by a complex lying upon or in a top portion of a layer inert particles, a weakly positive reaction is indicated by a complex located within a lower portion of the layer of inert particles, and a negative reaction is indicated by the absence of a complex, with the carrier bound material lying beneath the inert particles.

37 Claims, 2 Drawing Sheets

U.S. PATENT DOCUMENTS

| | | | |
|---|---|---|---|
| 3,905,772 | 9/1975 | Hartnett et al. | 422/72 |
| 4,105,415 | 8/1978 | Lovett | 23/292 |
| 4,108,972 | 8/1978 | Dreyer . | |
| 4,391,780 | 7/1983 | Boris | 422/104 |
| 4,608,231 | 8/1986 | Witty et al. | 422/102 |
| 4,659,658 | 3/1987 | McCarthy et al. | 436/534 |
| 4,677,080 | 6/1987 | Finkelstein et al. | 436/534 |
| 4,713,348 | 12/1987 | Ullman | 436/501 |
| 4,789,545 | 12/1988 | Woods et al. | 424/101 |

OTHER PUBLICATIONS

Fudenberg et al. (ed), *Basic and Clinical Immunology* (3rd edition), Lange Medical Publications, Los Altos, Calif. (1980), pp. 373–376 and 398–404.

Fisher Scientific Catalog (1983), pp. 180–184, 187–189 and 694.

Stedman's Medical Dictionary (24th edition), Williams & Wilkins, Baltimore, p. 770.

Lehninger, *Biochemistry*, Worth Publishers, Inc., New York, N.Y. (1970), pp. 141–143.

Tietz, *Fundamentals of Clinical Chemistry*, W. B. Saunders Company, Philadelphia, Pa. (1970), p. 234.

FIG. 1(a)      FIG. 1(b)      FIG. 1(c)
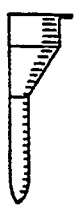   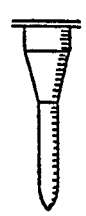
FIG. 2a         FIG. 2b
   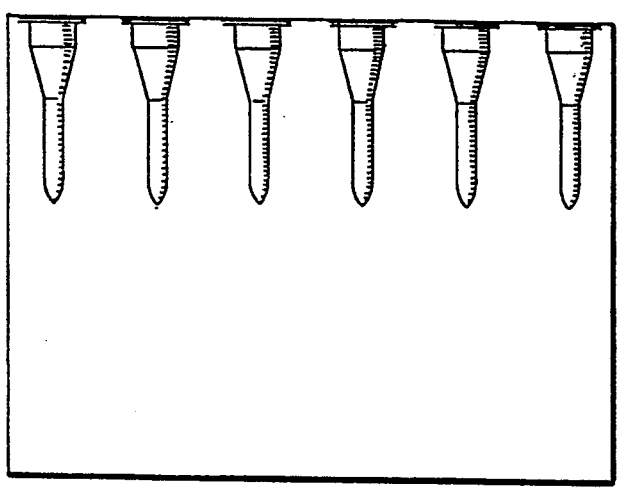
FIG. 3a         FIG. 3b
        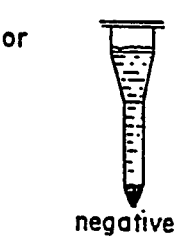
Serum and blood → Incubation → Centrifugation → Results
positive   or   negative
FIG. 4

FIG. 5

| A | B | AB | D | D$^u$ | Contr. |

Patient: _____
Id No: _____ Date: _____
Lot No: _____ Exp. date: _____

FIG. 6

| C | c | E | e | K | Contr. |

Patient: _____
Id No: _____ Date: _____
Lot No: _____ Exp. date: _____

FIG. 7

| A1 | A2 | B | I | II | Contr. |

Patient: _____
Id No: _____ Date: _____
Lot No: _____ Exp. date: _____

METHOD AND CARD FOR DETECTING ANTIGENS AND/OR ANTIBODIES

This application is a continuation of application Ser. No. 684,459 filed Apr. 11, 1991, now abandoned, which is a continuation of Ser. No. 122,152, filed Nov. 11, 1987, now abandoned.

This invention relates to biological test methods, and more particularly to a method of detecting antibodies or antigens, of the type wherein complexes of carrier-bound antibodies with antigens or of carrier-bound antigens with antibodies in an aqueous medium are made optically visible, using inert particles such as polyacrylamide gel particles. The invention further relates to test kits for detecting antigens and/or antibodies according to the aforementioned method.

Carrier-bound antigens and antibodies are routinely utilized for a multitude of analytical determinations. In this connection, a distinction is generally made between two principles:

(a) The antigen or antibody is bound to a solid carrier, such as small glass or plastic test tubes, glass or plastic beads, glass or plastic plates, paper, etc., and the liquid containing the antibody or antigen to be identified is added. If, after a certain reaction time, the latter react with the bound antigen or antibody, they are bound to the carrier and can, at least by means of a further reaction, be made measurable. As a rule, this takes place by labeling the antibody or antigen with radioactive, fluorescent, or enzymatically active tagging substances. A drawback of this method is that it is trouble-prone. Since washing is necessary after each reaction, insufficient washing or insufficient removal of the washing solution can falsify the results. Moreover, this method is hardly applicable to natural, carrier-bound antigens on erythrocytes, leukocytes, platelets, and other natural cells because of their size.

(b) Another principal method consists in binding the antigen or antibody to small particles such as latex or erythrocytes. After a certain reaction time with the antibody or antigen to be identified, the evaluation takes place on the basis of the agglutination pattern. Unlike the method described under (a) above, antigens and antibodies on erythrocytes, leukocytes, or platelets can be identified by this method. Drawbacks of this method are that, especially in a weak concentration, it is hard to differentiate between agglutinated and non-agglutinated (free) particles. Moreover, free particles can easily be adsorbed on the reaction vessel or the agglutination pattern mechanically destroyed. A further source of error resides in the possible adhesion of free particles to one another, thus simulating an agglutination. All these eventualities can lend to a false evaluation.

European Published Application No. 0 039 195 describes an antibody detection method wherein erythrocytes in negatively charged form are used in an isotonic solution of low ionic strength. A polymer in solution is added as an aid to agglutination. The agglutination is observed visually, preferably under a microscope. The agglutinate can be dissociated again by adding a solution of citrate and sugar.

It is an object of this invention to provide an improved method of detecting antibodies or antigens which is simpler than the prior art methods and free of their drawbacks.

Another object of this invention is to provide such a method in which readings can be taken easily and reliably.

To this end, in the method according to the present invention, a solution containing an antibody or an antigen is brought into contact with a carrier-bound antigen or antibody, respectively, a slurry or suspension of inert particles being added before, during, or after this reaction; upon formation of an antigen-antibody complex, the latter lying upon the sediment of the inert particles in the strongly positive case and being present within the inert particles in the weakly positive case; and in the absence of an antigen-antibody complex, i.e., in the negative case, the carrier-bound antibodies or antigens lying beneath the inert particles sediment.

The test kit according to the present invention contains at least one reaction vessel, inert particles, and one carrier-bound antibody and/or antigen per reaction vessel.

The chemical composition of the inert particles used in the method is not critical. The term "inert" is intended to mean that the particles must not enter into any unspecific reactions with the antigens or antibodies. Preferably, such inert porous particles as are available in commerce for liquid or gas chromatography will be used. These are products on the basis of cross-linked polymers, such as agarose, polyacrylamide, polydextran, or styrene-divinylbenzene polymers (e.g., "Sephadex," "Sepharose," or "Sephacryl," sold by Pharmacia AB, Uppsala, Sweden; or "Bio-Gel," sold by Bio-Rad Laboratories, Richmond, Calif.). Porous glass or silica gel also enters into consideration. The particle size is preferably from 10–200 microns. Those skilled in the art can determine by means of simple preliminary tests whether the particles are usable for a certain method of determination. As in the case of the above-mentioned inert particles, the type of carrier for the antigen or antibody is also not critical. For visual or optical-automatic measuring methods, it should be colored by nature (e.., erythrocytes). However, the carriers may also be tagged by means of a stain (e.g., latex, polymerized agarose). Other marking systems also enter into consideration, such as isotope, fluorescent, or enzyme labeling. These naturally require an appropriate measuring method. Moreover, the carriers are preferably likewise in particle form, the artisans or antibodies being bound to their surfaces.

The antigens and antibodies are preferably bound to these particles by chemical bonding, the type of bonding not being critical. Certain antigens, such as those of erythrocytes and platelets, already exist bound to these carriers. Leukocytes and platelets may be stained by known methods, if need be.

In the case of leukocytes or platelets, the inert particles may alternatively be stained. In that event, the reading zone is whitish, and the inert particles are colored.

According to the method of the present invention, it is possible to determine the free antigens or antibodies, certain carrier-bound antibodies or antigens, respectively, having to be given. Conversely, the carrier-bound antigens or antibodies may also be determined, the free antigens or antibodies, respectively, having to be given. The reaction vessels used for carrying out the method are, as a rule, small test tubes or microtiter plates of glass or plastic. The material is not critical.

The small test tubes may be either rounded or pointed, the shape being chosen as a function of the reading technique and the technical separation method and the quantity of material.

For carrying out the method of the present invention, small tubes or microreaction vessels are preferably used. Any desired number of these may, for example, be arranged side by side on a card. There may be an additional vessel, e.g., for preparing a test dilution or test suspension. The vessels and cards may be of plastic, such as PVC/PVDC, PET, or polystyrene. The vessels may, for instance, be made by the blister method, by a welding process, or by gluing. The vessels may contain the inert particles or industrially prepared reaction solutions. Since the invented method preferably includes a centrifuging step, special, suitable centrifuge heads must be used for the tubes or the cards with the containers. With one advantageous centrifuge head, at least 12 cards having, for example, six reaction vessels can be centrifuged simultaneously. In this case, 72 test can be carried out parallel to one another.

Although sedimentation can be brought about by allowing the vessels to stand and taking advantage of the force of gravity, it is more advantageous to use the centrifuging method since the desired sedimentation can be achieved after only a short time. The optimum conditions (centrifuging time and number of g) must be ascertained for each analysis system since the specific gravity, size, shape, deformability, and stability of the carrier-bound antigen-antibody complex, of the non-complexed, carrier-bound antibodies and antigens, and of the inert particles have an influence which is difficult to calculate.

BRIEF DESCRIPTION OF THE DRAWINGS

Certain aspects of the invention will now be described in detail with reference to the accompanying drawings, in which:

FIGS. 1(a)–(c) are diagrammatic elevations of three test tubes showing the patterns occurring in positive, weakly positive, and negative reactions, FIG. 2a is a side elevation and a FIG. 2b is front elevation of a typical microtube suitable for affixing to a card, FIGS. 3a and 3b are a side elevation and a front elevation, respectively, of a card with six small test tubes as in FIG. 2, FIG. 4 is a diagram of the way in which the test is carried out, and FIGS. 5, 6, and 7 are elevations of test cards for typical routine clinical tests.

Theoretically, the method according to the present invention can be used to test a sample of liquid for an antigen or an antibody which is specific to a known antibody or antigen, respectively. Either the known antigen or antibody, or the unknown antibody or antigen, must be bound to a carrier, e.g., an erythrocyte. The method of detection is based upon the realization that carrier-bound antigens and antibodies have different centrifugation properties from carrier-bound antigen-antibody complexes. If an antigen-antibody complex on a carrier is centrifuged together with a suspended, inert carrier material, the carrier-bound complex lies on the inert particles. If no reaction has taken place, only a free, carrier-bound antigen or antibody is in the test tube with the inert, suspended material. After centrifuging, this antigen or antibody is situated beneath the layer of inert particles. In this way, the positive or negative antibody reaction can plainly be read visually. It is also possible to automate this reaction. Weakly positive reactions may also occur, in which case the carrier-bound antigen-antibody complex is situated within the layer of inert particles.

A pattern of a positive reaction is shown in FIG. 1(a). If the reaction is only weakly positive, i.e., if only a few antigen-antibody complexes are formed, the antibody can be detected in the upper part of the inert particles in the centrifuge glass; cf. FIG. 1(b). If, on the contrary, there is no antigen-antibody complex but only a carrier-bound, free antigen or antibody, the latter is deposited beneath the inert particles after centrifuging. This is shown in FIG. 1(c).

As already mentioned, although various types of reaction vessels may be used, one such as is depicted in FIG. 2 is preferred. A side view is shown on the left, and a front view on the right. This small tube is covered, thus making it possible for certain industrially manufactured reagents to be supplied directly in the small test tube. The test tube is suitable for affixing to a card, which may hold several tubes, e.g., as shown in FIG. 3, where there are six small test tubes. FIG. 3a is a side view of the test card, while FIG. 3b is a front view. By means of this arrangement, a direct comparison of parallel tests is made possible.

The test card may be made in various ways. For example, small tubes may be glued to a card or may form an integral part of the card, in the manner of blister packaging. A mixture of inert particles and antibodies or antigen may be hermetically enclosed in these tubes in a predetermined quantity by the manufacturer, in which case the tubes may be sealed by means of a welded-on film. Test kits manufactured in this way are easily handled and may be used in an automatic analysis method. In this case, the pipetting of specimens, identification, automatic reading, evaluation, print-out, etc., is controlled by means of electronic data-processing. A further advantage is that only very small specimens are necessary. For instance, with 10–50 $\mu l$ of blood, all clinically relevant antigens can be detected with small amounts of reagents. Microbatches are particularly important in the case of substances which cannot be prepared synthetically and are available only in limited quantities; e.g., with 1 ml of the Rh antibody C, 20 antigen determinations can be carried out by a conventional method, whereas 1000 determinations are possible with the present method. If the test system is appropriately prepared, the determinations are so easy to carry out, and the results so plainly readable, that the test can even be carried out by auxiliary medical personnel.

Since no special laboratories are necessary, the interval between diagnosis and the start of therapy can be considerably reduced.

The invention will now be explained in more detail by means of the following examples.

I. Blood Group Antigens (ABO System)

EXAMPLE 1—A Antigen (a) Preparation or inert particles suspension:

Five ml of "Sephacryl," S200 Gel (Pharmacia) is washed twice in saline solution. After centrifuging (5 min., 1250 g), the supernatant is discarded, and the sediment is filled up to 4.5 ml with isotonic imidazol buffer (0.014 mol/l of imidazol 0.85% NaCl), pH 7.6.

(b) Addition of antibody:

Five-tenths ml of anti-A is added to 4.5 ml of the above suspension. The suspension is mixed well and is ready for use in this form.

(c) Preparation of reaction vessels:

The above antibody suspension is placed in polyethylene micro-tubes (ET-29MM, sold by Milian SA, Geneva, Switzerland), 100 µl in each tube. The inert particles settle to the bottom of the tube within a few minutes.

(d) Test procedure:

Twenty µl of an app. 4% erythrocyte suspension of the unknown blood specimen in isotonic imidazol buffer, pit 7.0 (one part blood to nine parts buffer) is placed in the reaction vessel filled with the antibody suspension and centrifuged for 10 min. at app. 100 g (Digifuge GL 122 089 centrifuge, 800 rpm, sold by Heraeus, Hanau, West Germany).

(e) Evaluation:

If the tested blood belongs to blood group A ($A_1$ or $A_2$), the antigen-antibody complex lies upon the inert particles (FIG. 1a). If it belongs to the rare A subgroups $A_3$ or $A_x$, the complex is distributed between the inert particles (FIG. 1b). If the blood belongs to groups B or 0, no agglutination can take place, and the erythrocytes collect at the bottom of the tube beneath the inert particles after centrifugation (cf. Table 1).

TABLE 1

| Blood Group | $A_1/A_2/A_1B/A_2B$ | $A_3/A_3B/A_x$ | B/0 |
|---|---|---|---|
| Test | Positive (FIG. 1a) | Weakly positive (FIG. 1b) | Negative (FIG. 1c) |

Completely analogously to Example 1, the B antigen is determined with anti-B instead of anti-A. The H antigen can be detected with H lectin. $A_1$ is distinguished from $A_2$ by means of $A_1$ lectin. Example 1 admits of a multitude of variations of the inert particles, the buffer used, the reaction vessels, the centrifugation time, and the number of g. The origin of the antibodies-whether human, mamalian, whether polyclonal or monoclonal-is unimportant, provided the variations do not change the reaction on Image (FIG. 4).

II. Rh-System Blood Groups (D, Du, C, E, c, e, Cw)

EXAMPLE 2—E Antigen

The preparation of the reaction vessels (steps a–c) is as in Example 1. Instead of anti-A, anti-E is used, for example. (d) Test procedure:

Step (d) of Example 1 is modified in that an enzyme solution ("DiaBrom," sold by DiaMed AG Murten, Switzerland) is used instead of, the imidazol buffer. It is known that concealed Rh antigens can be exposed thereby. Fifty µl of blood is suspended in 0.5 ml of enzyme solution. After app. 5 min., 20 µl of this suspension is placed in the reaction vessel prepared as in steps (a)–(c) of Example 1 and centrifuged for 10 min. at 100 g.

(e) Evaluation:

If the blood specimen contains antigen E, the antigen-antibody complex rests upon the inert particles (Table 2). Is antigen E not present, the eythrocytes collect under the inert particles.

TABLE 2

| | E antigen present | E antigen absent |
|---|---|---|
| Test | Positive (FIG. 1a) | Negative (FIG. 1c) |

The other Rh antigens can be determined completely analogously by means of the appropriate antisera. The clinically important D-variant Du can be differentiated by varying the concentration of anti-D.

III. Antibodies

EXAMPLE 3—Reverse Test (Isoagglutinins) The reaction vessels are prepared as in Example 1 (steps a–c), except that imidazol buffer is substituted for the antibody.

(d) Test procedure:

Since antibodies are to be identified in this example, erythrocytes with known antigens are used, e.g., A, B, and 0 test erythrocytes. These are suspended in the known LISS solution (50 µl of blood and 2.0 ml of LISS). Fifty µl of serum or plasma of the unknown blood specimen are placed in each of three identically filled reaction vessels. One hundred, µ of the A-cell suspension in LISS (low ionic strength salt solution, Technical Manual of the American Association of Blood Banks, Ninth Edition 1985, 205) is added to the first tube, 100 µl of the B-cell suspension to the second tube, and 100 µl of the 0-cell suspension to the third tube. As in Examples 1 and 2, the suspensions are centrifuged for 10 min. at 100 g.

(e) Evaluation:

If the unknown specimen contains anti-A, the first tube is positive, the second and third tubes negative (Table 3).

TABLE 3

| | A cells | B cells | O cells |
|---|---|---|---|
| Test | Positive (FIG. 1a) | Negative (FIG. 1c) | Negative (FIG. 1c) |

If the specimen contains anti-B, the second tube is positive, the first and third negative. If the third tube is positive, and the first and second are positive or negative, the specimen contains antibodies which are not anti-A or anti-B but directed to other antigens which lie on the 0 cells. In the event, further investigation is necessary.

EXAMPLE 4—Antibody Screening Procedure (Coombs Test)

The preparation of the reaction vessels is as in Examples 1–3, except that Coombs serum (DiaMed AG) is added to the inert particles suspension. As Is well known, Coombs serum consists of anti-human-IgG and anti-complement C3 ($C3b+C3d$), as well as anti-IgM and anti-IgA, and is used for detecting and identifying, in serum from patients, antibodies directed to erythrocyte antigens. It is expedient first to carry out an antibody screening procedure in which 0 erythrocytes having a known antigen for clinically relevant antibodies are used. If the result is positive, identification by means of a cell panel takes place.

Test procedure:

Fifty µl of serum or plasma from the patient is placed in each well or funnel of one or more identical reaction vessels filled with Coombs serum suspension. One hundred μl of the 0-cell suspension (50 μl of blood in 2.0 ml of LISS) is added. The mixture is incubated for from 10–20 min. at 37° C., at room temperature, or at from 2°–8° C., depending upon the antibody sought, and centrifuged for 10 min. at 100 g. Reading takes place as the previous examples.

If the specimen contains an antibody against one or more erythrocyte antigens, the positive pattern of FIG. 1(a) appears. With weaker antibodies, the pattern is as in FIG. 1(b). Analogous to the above test procedure, the antibody discovered may be identified by means of a cell panel containing various antigens (e.g., products obtainable in commerce from Ortho, Raritan, N.J. Dads, Baxter, Miami, Fla. and DiaMed).

IV. Blood-Typing on a Card

EXAMPLE 5—Blood Group A, $R_1R_1$ (CCDee), Kell Negative, Control Negative

Typing can be done individually in small tubes, on microtiter plates, or on cards. In this example, blood-typing on cards designed for determining a patient's blood group is described. The preparation of the reaction vessels takes place as described above. The cards are shown in FIGS. 5-7.

V. Determination of Free Antigens or Antibodies Not Belonging to Blood-Group Systems The reactions in Examples 1–5, in which the antigen is bound to the erythrocytes by its nature, can be applied to free antigens or antibodies by binding the respective antibodies or antigens to fixed erythrocytes or other particles by known methods.

EXAMPLE 6—Rheumatoid Factor Test (a) Preparation of erythrocytes:

Five ml of goat's blood in 0.011 mol citrate buffer, pH 6, is washed three times in saline solution. The sediment is suspended with 5 ml of saline solution, mixed with 0.5 ml of 30% glutaraldehyde solution (E. Merck AG, Darmstadt, West Germany), and allowed to react for 24 hrs. at room temperature with stirring. The sediment is washed three times in saline solution, mixed with 0.5 ml of rabbit IgG (10 mg/ml), and incubated for 24 hrs. at room temperature with stirring. After washing three times in saline solution, an app. 40% suspension of the loaded erythrocytes in imidazol buffer is prepared.

(b) Test Procedure:

The reaction vessels are prepared as in Example 3. An app. 4% erythrocyte suspension is prepared with imidazol buffer. As in Example 4, 50 μl of serum from the patient is placed in the well of the test tube, and 20 μl of the 4% erythrocyte suspension is added. After about 10 min. incubation at room temperature, centrifuging takes place as usual. If time serum contains rheumatoid factors, the reaction pattern of FIG. 1(a) or (b) appears. If it is desired to ascertain the titer, the test is repeated with serum diluted accordingly (0.9% NaCl).

The foregoing test is naturally not limited to the rheumatoid factors; for example, hepatitis antigens could be detected after coupling of HBsAg antibodies. By coupling inactivated HIV virus or synthetically produced proteins thereof to the erythrocytes, HIV antibodies can likewise be easily deflected.

Based upon these examples, it is immediately apparent that other proteins, viruses, or bacteria, or antibodies thereof, can easily be determined by the same method.

What is claimed is:

1. A method of detecting an antibody in a fluid by an indirect Coombs test, said method comprising:
   providing a microreaction vessel containing a slurry of suspension of inert particles and Coombs serum, said vessel being substantially transparent and having an upper portion and a lower portion, said upper portion having a greater diameter or width than the lower portion, with a transition portion situated between the upper portion and the lower portion, said upper portion having a sealed, openable upper sample receiving end and said lower portion having a closed lower end;
   adding the fluid to the vessel;
   adding to the vessel a carrier bound antigen which specifically binds to the antibody to form an optically detectable binding complex, to form a mixture with the fluid, wherein said mixture is located generally above the inert particles;
   incubating the mixture of the fluid and the carrier-bound antigen to form an optically detectable binding complex between the carrier-bound antigen and antibody;
   centrifuging the vessel; and
   observing the location of any carrier-bound antigen-/antibody complex to determine the presence of the antibody, with a strongly positive reaction being indicated by the antigen-antibody complex lying upon or within a top portion of a layer of the inert particles, weakly positive reaction being indicated by the antigen-antibody complex located within a lower portion of the layer of inert particles, and a negative reaction being indicated by the absence of the antigen-antibody complex, with the carrier-bound antigen lying beneath the inert particles.

2. The method of claim 1, wherein the microreaction vessel is mounted on or forms part of a centrifugable card comprising a planar card member and a plurality of elongated microreaction vessels lying side by side along an upper portion of the card member, said card member having a lower identifying indicia-receiving portion.

3. The method of claim 2, wherein said inert particles have a particle size of from 10–200 microns.

4. The method of claim 3, wherein the inert particles are cross-linked polymers, glass or silica gel.

5. The method of claim 3, wherein the carrier is erythrocytes, leukocytes, platelets, latex particles or polymerized agarose.

6. A method of detecting an antibody in a fluid sample by an indirect Coombs test, said method comprising:
   providing a microreaction vessel containing a slurry or suspension of inert particles and Coombs serum;
   adding about 10–150 μl of at least one fluid sample to the vessel;
   adding to the vessel a carrier bound antigen which specifically binds to the antibody to form a binding complex;
   incubating a mixture of the fluid sample and the carrier-bound antigen to form a binding complex between the carrier-bound antigen and the antibody;

7. The method of claim 6, wherein said inert particles have a particle size of from 10–200 microns.

8. The method of claim 7, wherein the inert particles are cross-linked polymers, glass or silica gel.

9. The method of claim 7, wherein the carrier is erythrocytes, leukocytes, platelets, latex particles or polymerized agarose.

10. The method of claim 6, wherein the microreaction vessel is mounted on or forms part of a centrifugable card comprising a card member and a plurality of elongated microreaction vessels lying side by side along an upper portion of the card member, said card member having a lower identifying indicia-receiving portion.

11. A method of detecting target antibodies or antigens by reaction with specific binding partners thereto, wherein one of either the target or the binding partner is bound to a carrier and the other is unbound, a complex of the carrier-bound target and the binding partner, or of the target and the carrier-bound binding partner, forming an agglutinate which is optically detectable, said method comprising:

provinding a microreaction vessel, sized to receive at least one fluid sample of about 10–150 $\mu$l, containing a slurry or suspension of inert particles and the known unbound target or binding partner thereto, said vessel being substantially transparent and having an upper portion and a lower portion, said upper portion having a greater diameter or width than the lower portion, with a transition portion situated between the upper portion and the lower portion, said upper portion having a sealed, openable upper sample receiving end said lower portion having a closed lower end;

adding about 10–50 $\mu$l of a solution containing the carrier-bound target or binding partner to the vessel to form a target-binding partner complex which is carrier-bound and optically detectable;

centrifuging the vessel; and observing the location of the carrier-bound complex to determine the presence of the target antibody or antigen to be detected, with a strongly positive reaction being indicated by a complex lying upon or in a top portion of a layer of the inert particles, a weakly positive reaction being indicated by a complex located within a lower portion of the layer of inert particles, and a negative reaction being indicated by the absence of a complex, with the carrier-bound target or carrier-bound binding partner lying beneath the inert particles.

12. The method of claim 11, wherein said inert particles have a particle size of from 10–200 microns.

13. The method of claim 12, wherein the inert particles are cross-linked polymers, glass or silica gel.

14. The method of claim 11, wherein the carrier is erythrocytes, leukocytes, platelets, latex particles or polymerized agarose.

15. The method of claim 11, wherein the microreaction vessel is mounted on or forms part of a centrifugable card comprising a card member and a plurality of elongated microreaction vessels lying side by side along an upper portion of the card member, said card member having a lower identifying indicia-receiving portion.

16. A method of detecting analyte antibodies or antigens in a fluid sample by reaction with known antigen or antibody, respectively, binding partners exhibiting specific binding affinity thereto, wherein either the analyte or known antigens or antibodies are bound to a carrier, the complex of the carrier-bound antigen and the analyte antibody, or of the carrier-bound antibody and the analyte antigen, forming an agglutinate which is optically detectable, said method comprising:

providing a microreaction vessel containing a slurry or suspension of inert particles;

centrifuging the fluid sample and the binding partner in said vessel in the presence of the inert particles; and determining the presence of analyte antibodies or antigens by observing the location of any agglutinate, with a strongly positive reaction being indicated by an antigen-antibody complex lying upon a top portion of a layer of the inert particles, a weakly positive reaction being indicated by an antigen-antibody complex located within a lower portion of the layer of inert particles, and a negative reaction being indicated by the absence of an antigen-antibody complex with the carrier-bound antigen or antibody lying beneath the inert particles;

wherein the vessel is an elongated vessel having an upper open end and a lower closed end, with the vessel being transparent and having an upper sample receiving portion, a funnel-shaped transition portion, and a lower portion which contains the inert particles, the upper portion having a greater diameter or width than the lower portion with the transition portion being situated thereinbetween, said vessel being sized to receive a body fluid sample of about 10–150 $\mu$l.

17. The method of claim 16, wherein the microreaction vessel is mounted on or forms part of a centrifugable card comprising a planar card member and a plurality of elongated microreaction vessels lying side by side along an upper portion of the card member, said card member having a lower identifying indicia-receiving portion.

18. Method of claim 17, wherein the antibodies or antigens detected are antigens or antibodies of blood groups, with different microreaction vessels on the card detecting a different antigen or antibody of the $A_1$, $A_2$, $A_1B$, $A_2B$, $A_3$, $A_3B$, $A_x$, B, O, Du, C, E, c, e, or Cw groups.

19. Method of claim 18, wherein the antigen or the antibody is bound to erythrocytes.

20. The method of claim 16, wherein said inert particles have a particle size of from 10–200 microns.

21. The method of claim 16, wherein the inert particles are cross-linked polymers, glass or silica gel.

22. The method of claim 16, wherein the carrier is erythrocytes, leukocytes, platelets, latex particles or polymerized agarose.

23. Method of claim 16, wherein the carrier material is naturally colored or tagged.

24. Method of claim 16, wherein the carrier material is stained or is isotope, fluorescent, or enzyme labeled.

25. Method of claim 16, wherein the carrier material is erythrocytes, leukocytes or platelets.

26. Method of claim 16, wherein the inert particles are porous globules of polyacrylamide gel, of cross-linked dextran, of glass or of silica gel, having a particle size of from 10–200 microns.

27. The method of claim 16, wherein the antibodies or antigens detected are blood group antibodies or antigens.

28. The method of claim 16, wherein the antibodies are carrier bound and are antibodies against proteins, viruses, bacteria, or synthetically produced proteins.

29. The method of claim 16, wherein the antigens are carrier-bound and are components of body fluids.

30. The method of claim 29, wherein the body fluid is blood, serum components, or plasma components.

31. Method of claim 16, wherein the fluid sample is a blood specimen, and the antibody is specific for blood-group antigens.

32. Method of claim 16, wherein the micro reaction vessel contains antibodies for determining the presence or absence of Rh antigens in a blood specimen.

33. A centrifugable card for use in the determination of an antibody or antigen in a fluid sample, comprising a card member and a plurality of elongated microreaction vessels lying side by side along an upper portion of the card member, said card member having a lower identifying indicia-receiving portion therein, each said vessel being transparent and having a sealed, openable upper end and a closed lower end, an upper sample receiving portion, a funnel-shaped transition portion and a lower portion, said upper portion having a great diameter or width than the lower portion, with the transition portion situated therein between, each said vessel being sized to receive a fluid sample of about 10–150 $\mu l$ and containing in the lower portion a slurry or suspension of inert particles.

34. The card of claim 33, wherein each vessel contains Coombs serum or a specific binding partner to the antibody or antigen to be determined or semi-quantitated.

35. The card of claim 34, wherein each microreaction vessel of a card contains a different antibody.

36. The card of claim 33, wherein the inert particles have a particle size of from 10 to 200 microns.

37. The card of claim 33, wherein the inert particles are cross-linked polymers, glass or silica gel.

* * * * *